United States Patent [19]

Golden

[11] 4,354,503
[45] Oct. 19, 1982

[54] BLOOD PRESSURE CUFF

[76] Inventor: Richard I. Golden, 1736 Highland, Wilmette, Ill. 60091

[21] Appl. No.: 219,565

[22] Filed: Dec. 23, 1980

[51] Int. Cl.³ ............................................... A61B 5/02
[52] U.S. Cl. .................................... 128/686; 128/677; 128/327
[58] Field of Search ............................... 128/677–686, 128/327

[56] References Cited

U.S. PATENT DOCUMENTS

| 2,320,179 | 5/1943 | Gray ................................... | 128/686 |
| 3,977,393 | 8/1976 | Kovacic ............................. | 128/686 |
| 4,106,499 | 8/1978 | Ueda ................................... | 128/686 |

FOREIGN PATENT DOCUMENTS

| 2911260 | 10/1980 | Fed. Rep. of Germany ...... | 128/686 |
| 7502303 | 8/1976 | Netherlands ....................... | 128/686 |

Primary Examiner—Lee S. Cohen
Assistant Examiner—Angela D. Sykes
Attorney, Agent, or Firm—Bernard L. Kleinke

[57] ABSTRACT

A blood pressure cuff for sensing blood pressure in a limb of the body, is adapted to fit a large range of sizes of limbs, and enables the cuff to be secured snugly in place on the limb. The cuff includes an elongated flexible band having an inflatable bladder therein and having a strap at one end and a strip at the other end. The strip cooperates with an adjacent portion of the band to form a loop for threadably receiving the strap during the wrapping operation.

10 Claims, 4 Drawing Figures

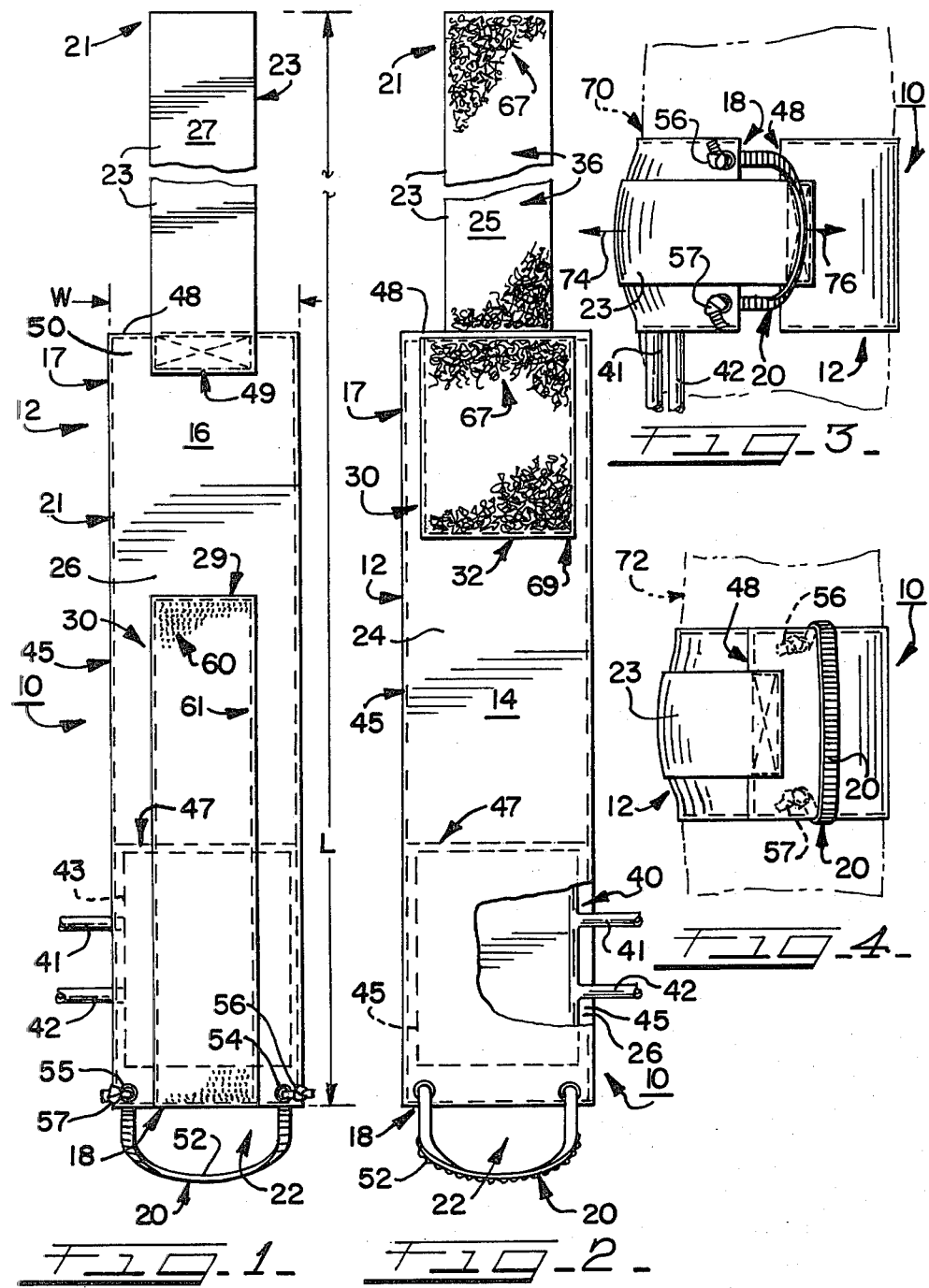

BLOOD PRESSURE CUFF

TECHNICAL FIELD

The present invention relates in general to blood pressure cuffs, and in particular to such blood pressure cuffs especially suitable for use in polygraphy.

BACKGROUND ART

Many different types and kinds of blood pressure cuffs have been known in the prior art. In use, prior known cuffs have been first positioned on a limb with the measuring area of the cuff—the area containing the inflatable bladder—placed against blood vessels of the limb. The cuff is then wrapped snugly around the limb and the ends of the cuff secured so as to hold the cuff in position on the limb during the measurement. The cuff is then inflated, and a reading of the blood pressure taken.

Blood pressure cuffs suffer from several significant problems, such as difficulty in providing a single cuff which can be fitted to a wide variety of sizes of limbs of greatly differing circumference, shifting of position of the cuff when it is tensioned and secured about a limb, and discomfort caused by the pressure of the cuff on a limb.

The problem of fitting limbs of widely differing size has been dealt with conventionally by providing an assortment of different size cuffs. However, in order to fit small children as well as substantially everyone else, including large adults, three or four different size cuffs are required. Thus, inventory problems are common. Also, sometimes the size of the limb is misjudged, and the conventional cuff must be removed and a different size cuff must be located and then applied to the limb. Such inconveniences are unwanted and are unduly time consuming.

The problem of shifting of the cuff occurs during the wrapping, tensioning and securing of a pressure cuff to a limb. Conventional cuffs oftentimes shift and become somewhat askew in their final wrapped position on the limb. Such improper positioning of the cuff on the limb may result in inaccurate blood pressure measurements. Additionally, when the cuff is askew in its final wrapped position, the cuff is not tightly secured in place. Especially in polygraphy, a loosely wrapped cuff adversely affects the sensitivity of the cuff to detect blood pressure, or relative changes in blood pressure when used with polygraph apparatus. The greater the wrap tension of the cuff, the better the coupling of the cuff bladder to the arterial vessels of the limb so that impulses of the cardiovascular system of the body are transmitted to the bladder with little loss of energy. Thus, an improperly wrapped cuff is much less sensitive for detecting blood pressure, or relative changes thereof in the body.

Pressure cuffs used with polygraph instruments are pressurized to a sufficiently high level to restrict severely the flow of blood in the limb, thereby producing a tourniquet effect. As a result, discomfort or pain, caused by compressed tissue, is directly proportional to the area of the compressed tissue and the applied pressure. Blotches or discolorations on the surface of the limb are oftentimes produced and are caused by ruptured blood vessels and by blood flowing back to the heart through body tissues rather than through the cuff-constricted veins. So grave are these problems that at least one state requires specific time limits, such as four minutes, on the length of time that a cuff may be pressurized during a polygraph test. If the pressure of the cuff is reduced to ameliorate these problems, the accuracy of interpretation of the subject's responses to questions may be adversely affected.

In an attempt to overcome the problem of pain and discomfort associated with the use of a pressure cuff in polygraphy, polygraph instruments have been employed, using low-pressure cuffs and electronic equipment for detecting blood pressure variations. However, such polygraph apparatus suffers from the problem that greater sensitivity may show up spurious minor variations in blood pressure and thus the readings may be difficult to interpret.

In an attempt to overcome some of the foregoing problems associated with conventional pressure cuffs, a prior known cuff was designed to reduce the shifting of position during affixing it to a limb, and to fit many different size limbs. In this regard, reference may be made to U.S. Pat. No. 3,977,393 issued to V. E. Kovacic. As mentioned in the foregoing patent, shifting of position during affixing to a limb is reduced by providing the cuff with an elongated slot or hole in the band intermediate its ends to enable one end to be threaded through the slot so that both ends may be grasped and tension applied in opposite directions to secure the cuff about the limb.

In order to fit different size limbs, the Kovacic cuff is accomplished by making the slot elongated, so that the cuff has a range of different circumferences, determined by the extreme ends of the slot.

However, the Kovacic cuff can be used only with limbs having circumference falling within a relatively narrow range of circumferences. Very large limbs cannot be accommodated due to the physical dimensions of the cuff. Limbs smaller in diameter than a limiting size imposed by the geometry of the slot of the cuff cannot be accommodated. In order to fit the cuff to a smaller limb, such as a child's or woman's limb, requires that the slot not be used. Instead, the cuff is wrapped in place about the limb, by overlapping the ends without the use of the double-tensioning feature. As a result, the cuff may shift, and inaccurate readings may result. Moreover, one may attempt to use the slot on a small limb, only to discover that the cuff cannot be tightened about the limb. Thus, the cuff must be removed entirely and be re-applied without the aid of the double-tensioning feature.

Therefore, it would be highly desired to have a pressure cuff, which fits many different size limbs in a single operation, which is easy to apply with little or no circumferential shifting, and which reduces greatly discomfort and discoloration associated with its use. Such a cuff should be relatively inexpensive to manufacture.

DISCLOSURE OF THE INVENTION

Therefore, the principal object of the present invention is to provide a new and improved pressure cuff which is adjustable to fit many different size limbs, and which can be applied in a simple manner with little or no shifting thereof for all sizes of limbs so that it can be properly aligned and positioned for subsequent use.

Another object of the present invention is to provide such a new and improved pressure cuff, which enables the traumatic effects caused thereby to be greatly reduced.

Briefly, the above and further objects of the invention are realized by providing a blood pressure cuff which includes an elongated flexible band having an inflatable bladder device disposed near one end of the band. A strip of material is connected fixedly to the band, transversely thereacross, near one end of the band to define with an adjacent portion of said band a loop for receiving the opposite end of the band. As a result, the band can be tightened about a limb by pulling on both of the ends of the band, and fastening devices on the band secure releasably the cuff in position on the limb.

The pressure cuff of the present invention can be attached very tightly and snugly about a limb in a convenient manner, without shifting the cuff during the application thereof, since tension can be readily applied to both ends of the band simultaneously. Moreover, the inventive cuff fits many different size limbs, such as the limb of a small child up to and including the thigh of a large adult human, and the cuff is applied in the same double-tension manner for all different size limbs.

Moreover, due to its unique construction, the cuff of the present invention is narrow in width as compared to conventional adult size cuffs, and therefore, is substantially less painful to use. In this regard, the pain or discomfort associated with the use of a pressure cuff is directly proportional to the area of the cuff overlying the skin tissue being compressed. Thus, a smaller cuff causes less pain. It should be noted that the Kovacic cuff is, by necessity, a wide cuff, to accommodate the opening therein. Also, a wider cuff has reduced sensitivity, since the larger amount of air in the bladder serves to dampen the response to the cardiovascular impules in a manner not unlike a pillow which cushions impulses.

BRIEF DESCRIPTION OF THE DRAWINGS

The above-mentioned and other objects and features of this invention and the manner of attaining them will become apparent, and the invention itself will best be understood by reference to the following description of an embodiment of the invention taken in conjunction with the following drawings, wherein:

FIG. 1 is a fragmentary plan view of the back face of the blood pressure cuff of the present invention;

FIG. 2 is a fragmentary plan view of the front face thereof with portions broken away for illustration purposes;

FIG. 3 is an elevational view of the cuff of FIG. 1 illustrating it wrapped in place on a large limb; and FIG. 4 is a elevational view of the cuff of FIG. 1, illustrating it wrapped on a small limb.

BEST MODE OF CARRYING OUT THE INVENTION

Referring now to the drawings and more particularly to FIGS. 1 and 2 thereof, there is shown a blood pressure cuff 10 which is constructed in accordance with the present invention. The cuff 10 comprises an elongated flexible band 12 of an overall length L, and an overall width W, having a front limb-engaging face 14, and a back face 16. The band 12 is adapted to be wrapped around a limb to measure blood pressure. At an end 18 of the band 12, there is fixedly attached a transversely extending flexible strip of material 20 which, together with the adjacent end portion of the band, defines a loop 22. At an opposite end 21 of the band 12 is attached an elongated flexible strap 23 having a front face 25 and a back face 27. The strap 23 is substantially more narrow than the width W of the band, and is adapted to be threaded through the loop 22 as hereinafter described in detail. A patch 29 on the back face 16 is a first part of releasable fastening devices generally indicated at 30. A patch 32 on the front face 14 is a second part of the releasable fastening device 30, and a patch 36 on the face 25 of the strap 23 is a third part of the fastening devices 30. The first and second parts are of a type which can be releasably interconnected to secure the cuff 10 on a limb.

As shown in FIG. 2, a conventional inflatable bladder shown fragmentarily at 40, having lines 41 and 42 connected in fluid connection with its interior, is contained in a compartment 43 of the band 12. After the cuff 10 is tensioned and secured about a limb, the bladder 40 is inflated via one of the lines 41 and 42 in a conventional manner, and the blood pressure is sensed and measured by a conventional pressure-measuring device (not shown) connected to one of the lines 41 or 42 as is well known in the art.

It is preferred that the ratio of length L to width W be from about four to one, to about seven to one, and that the width W be from about six to about twelve centimeters. It is even more preferred to provide a length-to-width ratio of from about five to one, to about seven to one, with the most preferred ratio being about six to one.

Considering now the cuff 10 in greater detail with reference to FIG. 1, the band 12 comprises an envelope 17 having two elongated panels, (a front panel 24 and a back panel 26) of flexible material stitched along their marginal edges at 45. The compartment 43 is formed in the envelope 17 by transverse stitching at 47. The lines 41 extend outwardly from the compartment 43 through gaps (not shown) in the stitching 45. The strap 23 is sewn at 49 to an end portion 50 of the envelope 17.

The strip 20 comprises a resilient ribbon 52 fixedly attached at its ends to the corner portions at the end 18 of the band 12 by passage through a pair of grommets 54 and 55 extending through holes in the corners of end 18, the ends of the ribbon 52 being knotted at 56 and 57. It is preferred that the resilient ribbon 52 be a rubber-clad nylon material. This material was found to provide a desirable combination of resilience, "stretchiness" and durability.

The loop 22 is suitably sized to permit the passage through it of the full width W of the envelope 17 without the necessity of folding or buckling about the longitudinal axis of the envelope 17 to allow easy passage through the loop 22. By providing a stretchy and resilient material, the strip 20 can be stretched outwardly in a convenient manner to facilitate the threading of the strap through the loop, when wrapping the cuff about a limb.

The patch 29 is comprised of Velcro material and carries on its face a plurality of hooks 60 which serve as bristles, and which comprise the first part of the Velcro two-part releasable fastening devices 30. The patch 29 is attached to the face 16 of the envelope 17 by stitching 61. The patch 32 is comprised of Velcro material having on its face loops 67 which serve as a soft fluffy material, and which are the second part of the Velcro two-part releasable fastening devices 30. The patch 32 is attached to the face 14 by stitching 69.

The front face 25 of the strap 23 is substantially continuous with and forms an extension of the face 14, and thus the patch 36 is substantially continuous and forms an extension of the patch 32. The patch 36 is comprised of Velcro material having loops 67.

Pressing together a loop surface and a bristle surface causes an intermeshing and interconnection releasably together of the Velcro parts. The strap 23 is comprised of a conventional fabric material, and the patch 36 is affixed to it by any suitable technique, such as by a suitable adhesive, or the like. Alternatively, the entire strap 23 may be composed of Velcro material.

Referring now to FIG. 3, the pressure cuff 10 is shown secured in place for measuring purposes on a limb 70 having a large periphery, which is greater than the length of the envelope 17 but less than the length L. To apply the cuff 10 to the limb 70, such as the bicep of an arm, the surface 14 is placed in contact with the limb 70 with the bladder 40 positioned over a blood vessel. The band is then wrapped around the limb 70 to encircle it, and the strap 23 is threaded through loop 22. The strap 23 is grasped and pulled in the direction indicated by the arrow 74, while, at the same time, the strip 20 is grasped and pulled in the direction indicated by the arrow 76. The strip 20 and the strap 23 are then pulled until the cuff 10 is tensioned very snugly in contact with the limb 70 in the final position of the cuff 10 on a limb 70 as shown in FIG. 3. It should be noted that since the limb 70 has a large periphery, the end 48 of the envelope 17 is spaced from and does not overlap its other end 18.

To secure the pressure cuff 10 on the limb 70, the patch 36 on the strap 23 is pressed firmly onto engagement with the mating patch 29, thus causing the loops 67 on the face 25 of the strap 23 to intermesh with the hooks 60 on the patch 29.

Thus, the cuff 10 is properly positioned on the limb ready for using in sensing blood pressure. After the blood pressure is sensed, the cuff 10 can be removed quickly and conveniently by reversing the operation. The patch 36 on the strap 23 is pulled away from the patch 29 to release the cuff so that the strap 23 can be backed out of the loop 22.

Referring now to FIG. 4, for small limbs, the steps described above are initially followed. However, with a small circumference limb, the ends 18 and 48 meet before the cuff 10 is snugly in place on the limb. The following steps are then carried out: the end 48 of the envelope 17 is threaded through the loop 22 and the entire width W of the envelope 17 of the cuff 10 is passed through the loop 22 in such a manner that the end 48 overlaps the end 18.

The size of the loop 22 is adjusted during the wrapping operation by merely pulling on the strip 20 to stretch it. The normal unstressed size of the loop 10 can be adjusted by varying the position of the knots 56 and 57 on the ribbon 52. It is preferred to adjust this size large enough to permit easy passage of the full width W of the envelope 17 of the cuff 10 without causing buckling of the cuff 10 along its longitudinal axis, yet small enough so that the ribbon 52 fits conveniently about the envelope as shown in FIG. 4. It has been found desirable to place a slight tension on the ribbon 52 by pulling on it when the envelope 17 is passed through it. Such tension helps center and hold the cuff 10 prior to its being secured in place.

The cuff 10 is then snugged and tensioned, in the same manner as previously described in connection with the application of the cuff 10 to a large limb as shown in FIG. 3. As shown in FIG. 4, the final relative positions of the ends 18 and 48 are overlapping and are not spaced apart.

It is important to note that the pressure cuff 10 is applied to both large and small limbs in a similar manner, and there is no need to judge, in advance, the size of the limb prior to wrapping the cuff about the limb. The cuff 10 can be applied to the arms of small children, and in a similar manner, to the thigh portion of the leg of an adult. In each case, tension is applied continuously to both end portions of the band during the wrapping operation to position properly and snugly the cuff in position.

The features of the present invention make it particularly suitable for use in measuring blood pressure with polygraph apparatus; however, it is also suitable for, and may advantageously be used in, other blood-pressure measuring applications, such, for example, as in the measurement of blood pressure for medical purposes.

While a particular embodiment of the present invention has been disclosed, it is to be understood that various modifications are possible and are contemplated within the true spirit and scope of the appended claims. For example, different types and kinds of materials such as plastics, fabrics or the like, and different types of releasable fastening devices, such as hooks and eyes and the like may be employed in connection with various portions of the pressure cuff. Also, the different components of the cuff of the present invention may be attached or fastened together by various fastening techniques, such as stitching, gluing, stapling, riveting and the like. There is no intention, therefore, of limitations to the exact abstract or disclosure herein presented.

I claim:

1. A blood pressure cuff adapted to be positioned on a limb of a body, comprising: an elongated flexible band having first and second ends, said band having a front face intended for placing in contact with the limb and having a back face, said band having a compartment therein; bladder means confined within said compartment and adapted to be inflated; fastening means having a first part disposed on said back face at one of said ends; said fastening means having a second part disposed on said front face at the other one of said ends; an elongated separate strip of material extending transversely across said band near said first part at said one of said ends to define, with an adjacent portion of said band, a loop for receiving the opposite end of said band so that said band can be tightened about the limb by pulling on both of said ends of said band and said first and said second fastening means parts interconnected for securing releasably the cuff in position on the limb; means attaching said strip to the said one end of said band for enabling said loop to be sufficiently large to receive said opposite end of said band without causing it to buckle; and an elongated flexible strap extending from the opposite end of said band and being adapted to extend through said loop when said band is tightened about the limb, said strap being narrower in width than said band to enable said strap and a portion of the opposite end of said band to be pulled through said loop to accommodate smaller size limbs; and said fastening means having a third part thereof on said front face of said band adjacent to the second part disposed on said strap so that said third part can interconnect with said first part of said fastening means when said opposite end of said band is pulled through said loop for accommodating small sized limbs.

2. A blood pressure cuff as recited in claim 1, wherein the ratio of the length of said band to the width of said band is between about four to one and about seven to one.

3. A blood pressure cuff as recited in claim 2, wherein said ratio is about six to one.

4. A blood pressure cuff as recited in claim 1, wherein said strip is composed of a resilient stretchable material.

5. A blood pressure cuff as recited in claim 4, werein said resilient stretchable material is a rubber-clad nylon material.

6. A blood pressure cuff as recited in claim 1, wherein said means attaching said strip to said band includes means defining a pair of spaced-apart holes therein, and the ends of said strip of material extend through said holes in said band and are secured in place.

7. A blood pressure cuff as recited in claim 6, wherein grommets are provided in said holes and said strip extends therethrough with said ends of said strip being knotted.

8. A blood pressure cuff as recited in claim 1, wherein said band includes an envelope having front and back elongated panels.

9. A blood pressure cuff as recited in claim 8, wherein said fastening means including Velcro devices.

10. A blood pressure cuff as recited in claim 9, wherein said width length is between about six centimeters and about twelve centimeters.

* * * * *